(12) United States Patent
Stearns

(10) Patent No.: US 6,714,674 B1
(45) Date of Patent: Mar. 30, 2004

(54) METHOD FOR CONVERTING DIGITAL IMAGE PIXEL VALUES

(75) Inventor: Charles Stearns, New Berlin, WI (US)

(73) Assignee: General Electric Company, Schenectady, NY (US)

( * ) Notice: Subject to any disclaimer, the term of this patent is extended or adjusted under 35 U.S.C. 154(b) by 913 days.

(21) Appl. No.: 09/070,486

(22) Filed: Apr. 30, 1998

(51) Int. Cl.$^7$ .................................................. G06K 9/00
(52) U.S. Cl. ..................................... 382/172; 382/169
(58) Field of Search ................................ 382/169, 170, 382/171, 172, 132, 128; 358/443, 453, 462; 250/583, 587

(56) References Cited

U.S. PATENT DOCUMENTS

| | | | | |
|---|---|---|---|---|
| 4,950,894 A | * | 8/1990 | Hara et al. ................... | 382/169 |
| 5,060,081 A | * | 10/1991 | Shimura ...................... | 358/443 |
| 5,164,993 A | * | 11/1992 | Capozzi et al. .............. | 382/132 |
| 5,239,378 A | * | 8/1993 | Tsuji et al. .................. | 382/169 |
| 5,305,204 A | * | 4/1994 | Ohhashi ...................... | 382/131 |
| 5,633,511 A | * | 5/1997 | Lee et al. .................... | 382/132 |
| 5,748,773 A | | 5/1998 | Tashiro et al. .............. | 382/169 |

FOREIGN PATENT DOCUMENTS

WO        WO89/12278        12/1989    ........... G06F/15/68

OTHER PUBLICATIONS

Schwenker, et al., Automatic Detection of the Useful Image Data From Digital X–ray Detectors, pp. 204–209, 1997, *Society for Photo–Optical Instrumentation Engineering*.

Schwenker, et al., Automatic Detection of the Useful Image Data From Digital X–ray Detectors, *Society for Photo–Optical Instrumentation Engineering*, vol. 3031, pp. 204–209, 1997.

* cited by examiner

*Primary Examiner*—Jingge Wu
(74) *Attorney, Agent, or Firm*—Fletcher Yoder

(57) ABSTRACT

A method is provided for converting values representative of pixel intensities from an input dynamic range to an output dynamic range. The input dynamic range is determined by acquisition circuitry, while the output range is determined by display or output devices or circuitry. A histogram of the input values is generated, and a lower limit value for the useful portion of the input range is identified from the histogram. An upper limit of the useful input range is then identified based on a log-transformed histogram computed from the original histogram, and on a threshold value located based on the lower limit value. Conversion of the pixel values is then performed by reference to the lower and upper limit values. The technique facilitates compensation for variations in utilization of the input dynamic range, and appropriately scales the input range utilized to the available output range.

20 Claims, 3 Drawing Sheets

METHOD FOR CONVERTING DIGITAL IMAGE PIXEL VALUES

TECHNICAL FIELD

The present invention relates to digital imaging and, more particularly, to the conversion of a range of input pixel values to a different range of output pixel values representative of an image, such as an X-ray image.

BACKGROUND ART

Discrete imaging devices, such as digital X-ray imaging systems, employ a detector which divides regions of an image into individual picture elements, or pixels. The array or matrix of pixels defines, when viewed as an overall image, features of interest, such as internal anatomy of a subject positioned adjacent to the detector. To facilitate interpretation by physicians and technicians, the individual intensities of the pixels typically define the features of the image by imitating contrasts and textures obtainable through conventional film-based X-ray or imaging systems.

To convert the detected pixel intensities to digitized values suitable for display, the pixel intensity values are processed after acquisition by the detector. In a first stage, the detected pixel intensities are digitized in values which vary over a predetermined dynamic range of the detector and acquisition circuitry, such as 12 to 14 bits. In X-ray systems, for example, these digitized values are representative of the quantity of X-rays received by each pixel during data acquisition. Subsequently, the pixel intensity values are scaled to map the values onto the dynamic range of a display device. As part of this scaling, it is common to perform logarithmic transformation of the image pixel values to obtain a resulting image which mimics conventional film-rendered images. In addition, the scaling process maps the dynamic range of the detector and acquisition circuitry onto the dynamic range of the display. The latter range may be substantially different from that of the upstream circuitry, such as on the order of 8 to 10 bits.

While the logarithmic transformation of the digitized pixel values is useful in rendering an image which is understandable by attending physicians and technicians, performing the transformation prior to the dynamic range scaling can be problematic. For example, histograms are often employed to analyze pixel intensity values. However, processing of histograms generated based on the transformed values can result in difficulties in identifying high and low limits of relevant portions of the detected data, rendering the dynamic range scaling difficult. The use of logarithmically transformed data prior to dynamic range scaling can also result in loss of accuracy for individual pixels in the image matrix.

There is a need, therefore, for an improved method for processing discrete image data that facilitates use of as much of the dynamic ranges of acquisition circuitry and display circuitry as possible. In particular, there is a need for an improved method for converting digital pixel values defining a discrete pixel image from a first dynamic range to a second dynamic range in a computationally efficient manner.

DISCLOSURE OF THE INVENTION

In an exemplary embodiment of the invention, digitized values for a plurality of pixels of an image, such as an X-ray image, are converted from a first dynamic range to a second dynamic range for eventual display of the overall image. The input values, distributed over the first dynamic range, are used to form a histogram representative of the number of pixels having predetermined digital intensity values. A lower limit of the relevant portion of the input data dynamic range is identified from the histogram. A transformed histogram is developed based upon the input value histogram. The transformed value histogram is used to determine a threshold value for the log-transformed image. Based upon this threshold value, an upper limit of the relevant portion of the input data range is identified from the transformed value histogram. With the lower and upper limits of the input value dynamic range thus identified, the input pixel values are mapped onto output values over the second dynamic range.

The technique offers a computationally efficient approach to mapping of input and output dynamic ranges in image processing, particularly in digital X-ray systems. By identifying the low and high limits of the input dynamic range, the useful range of the input values is identified and the mapping is performed over this useful range. The technique may be employed for individual images, thereby accommodating variations in intensity values for individual patients and individual images. The resulting images provide consistent appearance, facilitating comparison and interpretation of imaged features.

BEST MODE FOR CARRYING OUT THE INVENTION

Figure 1:
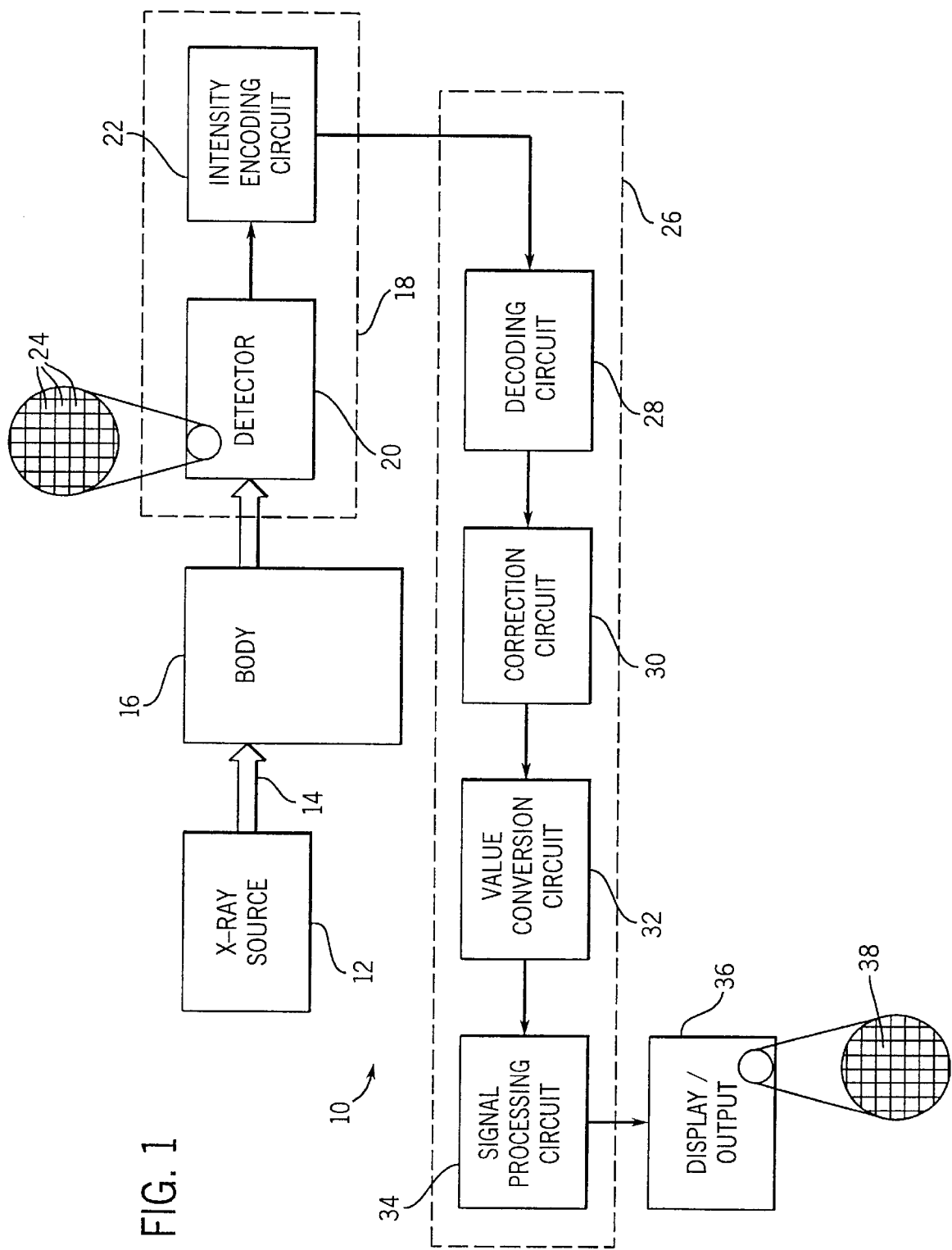
FIG. 1 is a diagrammatical representation of an X-ray imaging system including circuitry for converting input values for individual pixels of an image into output values for display.

Referring now to FIG. 1, an imaging system 10 is illustrated in the form of an X-ray system. It should be noted, however, that the technique disclosed herein is not limited to use in such X-ray systems, but may find application in other types of digitized image processing modalities. Imaging system 10 includes a X-ray source 12 configured to emit a stream of X-rays 14. When an image is to be captured, a subject, such as a human body 16 is positioned between the X-ray source 12 and an image acquisition unit 18. Image acquisition unit 18 includes a detector 20 and an intensity encoding circuit 22. A portion of the X-rays emitted by the source 12 pass through the body and strike the detector 20.

Detector 20 is configured to divide the surface receiving the X-rays into a matrix of discrete picture elements or pixels 24. Detector 20 outputs a stream of data signals representative of the intensity of radiation received by each of the discrete pixel locations. Intensity encoding circuit 22 receives the data signals from detector 20 and encodes the intensity levels in a data stream in which the intensity, level or value of each pixel is assigned a digitized value over a predetermined dynamic range. For example, intensity encoding circuit 22 may digitize the intensity values over a dynamic range of 12 to 14 bits per pixel, providing $2^{12}$–$2^{14}$ different digitized intensity values potentially assignable to each pixel.

Signal receiving unit 18 then transmits these encoded values to an image processing unit 26 for further refinement. Image processing unit 26 includes circuitry configured to process the digitized values and to render output data which can be displayed in a form comprehensible to an attending physician or technician. In the diagrammatical illustration of FIG. 1, image processing unit 26 includes a decoding circuit 28, a correction circuit 30, a value conversion circuit 32, and a signal processing circuit 34. Decoding circuit 28 receives the digitized values from intensity encoding circuit 22 and partially decodes the information, such as by placing the pixel values in a desired order or sequence, as will be appreciated by those skilled in the art. Circuit 28 then transmits the decoded values to correction circuit 32 which performs corrections on the values, such as to produce digital intensity values which are linearly proportional to the quantity of X-rays received in each pixel location of detector 20 during the acquisition process. As will be appreciated by those skilled in the art, correction circuit 30 may perform various corrections on the values, such as to normalize the values to produce, optimum, consistent presentations of images acquired by the system, thereby compensating for such factors as the size of the patient, the composition of the tissues or structures of the body, the X-ray dosage, and so forth.

The corrected digital intensity values are then transmitted to value conversion circuit 32. Value conversion circuit 32 converts the digital intensity values from the range output by intensity encoding circuit 22 to a range appropriate for display, as summarized below. These converted values are then further processed by signal processing circuit 34, which may perform such functions as enhancing structural details, smoothing texture, and so forth. Signal processing circuit 34 then outputs values for the digitized image to a display/output device 36, typically including a monitor or printer capable of producing a discrete pixel image 38 representative of the features of interest within body 16.

Value conversion circuit 32 accommodates differences in the dynamic ranges of values output by signal receiving unit 18 and values needed by display/output device 36. For example, while pixel intensity values output by unit 18 may have a dynamic range of 12–14 bits per pixel, the input range of display/output device 36 may be smaller, on the order of 8–10 bits per pixel. To permit both acquisition and display circuitry to utilize the greatest portion of their respective dynamic ranges, then, value conversion circuit 32 analyzes the useful portion of the dynamic range of the incoming digitized values, and, based upon this useful portion, converts the incoming digitized values to the dynamic range required by display/output device 36.

It should be noted that certain of the functional circuitry illustrated in FIG. 1, including correction circuit 30 and value correction circuit 32, may be embodied in appropriate code within a general purpose or application-specific microprocessor or computer. Moreover, the microprocessor or computer may serve to carry out other functions and signal processing operations beyond those described herein.

Figure 2:
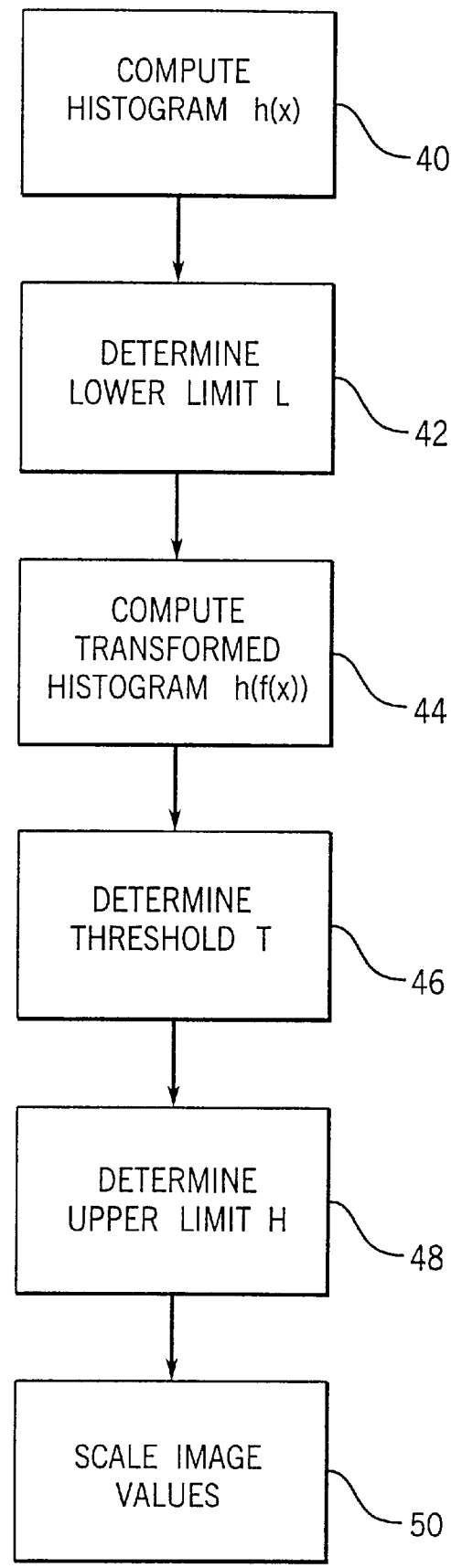
FIG. 2 is a flow chart illustrating steps and exemplary control logic for converting or scaling digitized pixel values over a first dynamic range to values over a second dynamic range for display.

FIG. 2 represents steps in exemplary control logic implemented by value conversion circuit 32 in determining the useful portion of the incoming digitized image pixel values and in converting or scaling these values to the dynamic range of downstream circuitry. As illustrated in FIG. 2, once value conversion circuit 32 receives the digitized signals representative of pixel intensities, a histogram h(x) is generated to determine pixel populations having individual intensity values over the full input dynamic range. A schematic illustration of a histogram of this type is illustrated in FIG. 3.

Figure 3:
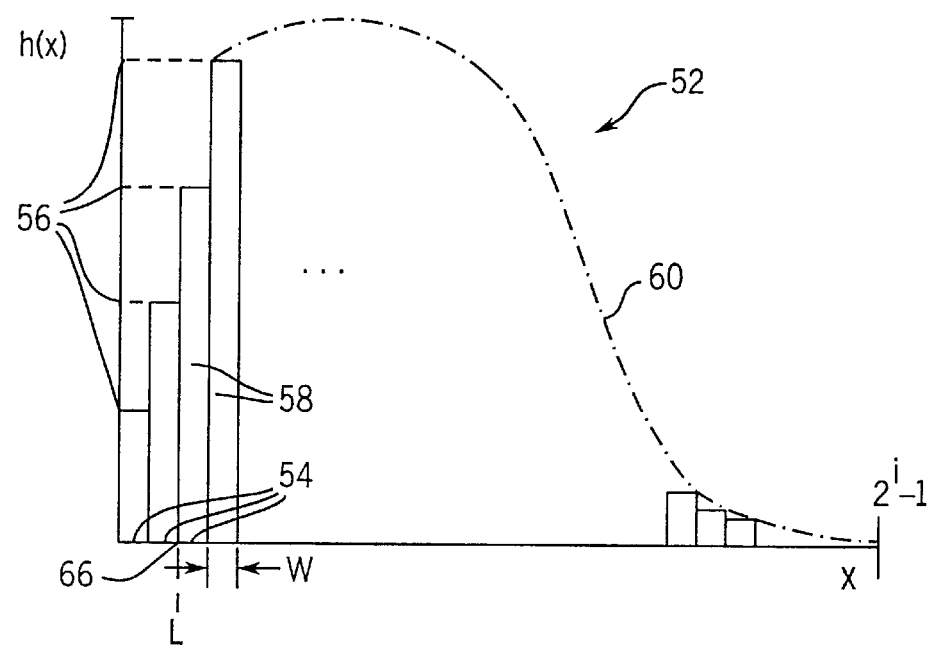
FIG. 3 is an exemplary histogram of pixels having predetermined intensity values for an image detected via the system of FIG. 1 in accordance with the logic of FIG. 2.

As shown in FIG. 3, the histogram 52 may be represented graphically by plotting intensity values 54 across a horizontal axis, and population counts 56 for each of the intensity values along a vertical axis. The resulting graphical representation forms bars 58 which define a distribution curve 60 in a stepwise manner. Each bar 58 has a width W such that the entire dynamic range is defined over the horizontal axis between a digitized value of zero bits to a maximum value of $2^I-1$ bits, where "i" represents the number of bits in the input dynamic range. It should also be noted that the sum of the population counts for all of the intensity values equals the total population of the pixels considered in the image.

While certain images may include pixels having intensities over most of the useful input range (0 to $2^I-1$), value conversion circuit 32 analyzes the input values to determine the useful portion of the dynamic range over which the values lie. Thus, where variations in the acquisition process result in utilization of less than all of the input dynamic range, the converted values will nevertheless provide as much information as is available from the input values.

In a first step in this process, as indicated by step 42 in FIG. 2, circuit 32 determines the lower limit L of this useful range. This step is graphically represented in FIG. 3. In FIG. 3, reference numeral 62 indicates an exemplary lower limit L established by reference to histogram 52. The lower limit value is selected by locating an intensity value along the horizontal axis below which a desired percentage of the global pixel population falls. That is, beginning with an intensity value of zero, the pixel counts 56 of bars 58 for each intensity value are accumulated until the desired pixel population percentage is obtained. Once the percentage is reached, the lower limit is set at the next higher intensity value. In general, lower limit values corresponding to 0.5 to 1 percent of the global pixel population have been found to provide satisfactory results.

Figure 4:
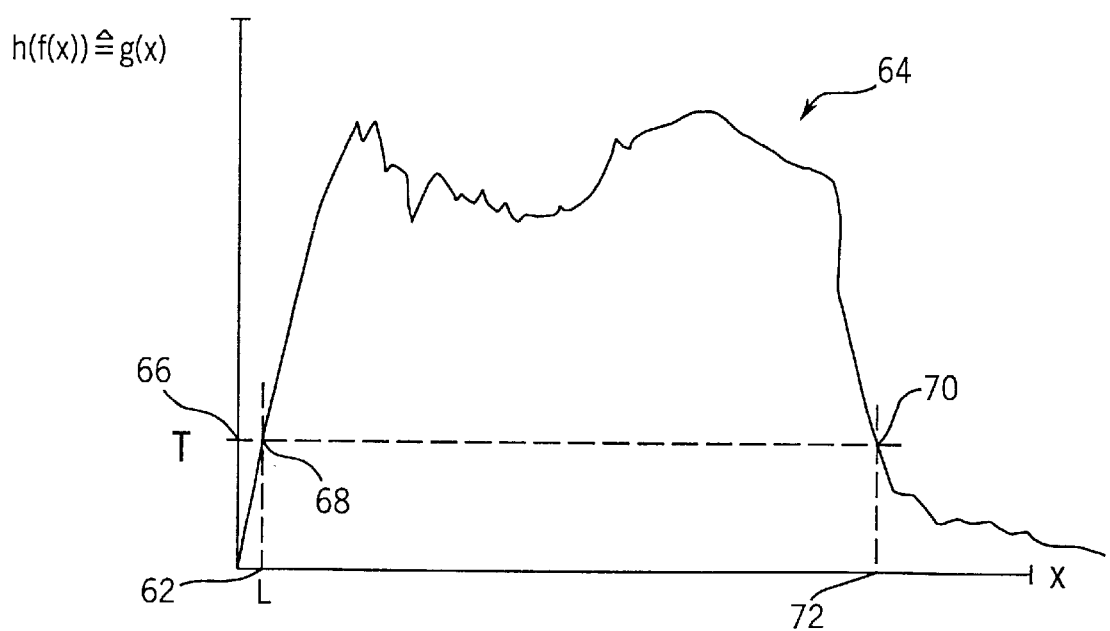
FIG. 4 is an exemplary histogram of transformed pixel values generated based on the histogram of FIG. 3, in accordance with the logic summarized in FIG. 2.

Referring again to FIG. 2, once the lower limit L has been identified, a log-transformed histogram h(f(x)), defined as g(x), is calculated as indicated at step 44. An exemplary log-transformed histogram 64 is illustrated in FIG. 4. The log-transformed histogram may be generated from the equation:

$$h(f(x))=x\ h(x);$$

where the values of x and h(x) are based upon the values of the pixel intensity histogram 52 of FIG. 3. The log-transformed histogram may be smoothed using a low-pass filter technique, such as by local averaging of the population counts for each intensity value with the immediately preceding and succeeding population counts. Such filtering tends to smooth peaks and valleys which may occur in the histogram profile.

Once the log-transformed histogram g(x) has been established, a threshold value T is determined, as indicated at step 46 in FIG. 2. Referring again to FIG. 4, the threshold value T is located from the log-transformed histogram 64 by identifying a value of g(x), as indicated by reference numeral 66, at which the lower limit value T, indicated by numeral 62, intersects the log-transformed histogram, as indicated at intersection point 68 in FIG. 4. The histogram 64 is then scanned from the value x=L until a second intersection point 70 is located at which the histogram value g(x) falls below the threshold value T. This value will form the basis for establishing an upper limit for the useful portion of the input dynamic range.

Before establishing the upper limit value, however, a verification comparison is preferably performed to determine whether a satisfactory portion of the dynamic range has been selected through use of the threshold value T. In particular, a comparison of the identified value 72 and a multiple of the lower limit value has been found to provide a satisfactory test of the width of the dynamic range. For example, if the value identified at 72 is determined to be less than 2L, the algorithm may be considered to have found a spurious feature of the histogram, requiring use of a different threshold value T. In such cases, the threshold value is reset to a lower value, such as 0.8T, and the foregoing procedure is performed using this reduced threshold to identify a value 72 further along the histogram 64.

As indicated by step 48 in FIG. 2, based upon the value 72, an upper limit value H for the useful portion of the input dynamic range is next determined. The value of H is set to a multiple of the value 72 determined as summarized above. It should be noted that this multiple need not be an integer multiple, and will, in general, differ for various types of modalities and subjects. For example, in digital X-ray imaging systems, the multiple of the value 72 used to set the upper limit H will differ in accordance with a need to view the skin/air interface, lung interstitium, or other details. By way of example, in chest radiographs, a multiple of 1.5 has provided good results over a range of images.

With the lower and upper limits of the useful portion of the input dynamic range thus determined, value conversion circuit 32 next scales the pixel values from the input range to the output range as indicated at step 50 in FIG. 2. In the presently preferred technique this conversion is performed in accordance with the following relationship:

$$Output = (2^b - 1) - \left\lfloor (2^b - \varepsilon) \frac{\log(Input)/L}{\log(H/L)} \right\rfloor$$

where the value Output is the scaled output value for each pixel, Input is the corresponding input value for the pixel, b is the number of bits in the output dynamic range, $\varepsilon$ is small number (less than or equal to 1.0, and typically 0.5) used to assure that the output value does not go below zero, and L and H are the lower and upper limit values, respectively. The brackets represent the operation of determining the largest integer value less than or equal to the real-valued quantity enclosed therein. Note that the transformation described by this equation reverses high and low pixel values, such that pixels receiving low input values will have high output values (resulting in inversion of light and dark pixels in the resulting image). This transformation is appropriate, for example, in images such as chest radiographs. However, as will be appreciated by those skilled in the art, other transformations which do not reverse high and low values may be appropriate in other applications.

It has been found that the foregoing method provides satisfactory conversion of input values to output values in a computationally efficient manner. Moreover, the procedure is readily adaptable to various imaging modalities, as well at to a wide variety of input and output circuitry having substantially different dynamic ranges. Finally, the method automatically accommodates variations in the bandwidth of the dynamic range actually utilized, even in particular images produced by a single imaging system or on a particular subject, providing more consistent and comparable images, and thereby facilitating image interpretation and analysis.

What is claimed is:

1. A method for converting digitized image pixel values from a first range to a second range, the method comprising the steps of:
   (a) determining a lower limit value of a relevant portion of the first range based upon non-log transformed pixel values;
   (b) generating an intensity histogram representative of pixel populations having specified intensities, and transforming the histogram to generate a log-transformed histogram;
   (c) identifying a threshold value for an upper limit of log-transformed values from the log-transformed histogram;
   (d) identifying a population of pixels having log-transformed values having a desired relationship to the threshold value;
   (e) determining an upper limit value of the relevant portion of the first range based upon the identified population; and
   (f) converting the non-log transformed pixel values to converted values over the second range based upon the lower and upper limit values.

2. The method of claim 1, wherein the population identified in step (d) is a population having log-transformed values lower than the threshold value.

3. The method of claim 1, wherein the lower limit value is determined based upon populations of pixels identified in the intensity histogram.

4. The method of claim 3, wherein the upper limit value is determined based upon the log-transformed histogram and the population identified in step (d).

5. The method of claim 1, wherein the threshold value corresponds to a desired log-transformed value.

6. The method of claim 5, wherein the population identified in step (d) is identified by comparison of the threshold value to log-transformed values in the log-transformed histogram.

7. The method of claim 1, including the further steps of comparing the population identified in step (d) to a desired population size, and resetting the threshold value based upon the comparison.

8. The method of claim 7, wherein the desired population size is determined based upon a population of pixels having a predetermined relationship with the lower limit value.

9. A method for converting digitized image pixel values from an input dynamic range to an output dynamic range, the method comprising the steps of:
   (a) generating a first histogram of non-log transformed pixel values in the input dynamic range;
   (b) identifying a first limit value for the pixel values in the input dynamic range from the first histogram;
   (c) generating a second histogram of log-transformed values of the pixel values by transformation of the first histogram;
   (d) identifying a population of pixels having desired log-transformed values from the second histogram;
   (e) identifying a second limit value for the pixel values in the input dynamic range based upon the identified population; and
   (f) converting the non-log transformed pixel values from the input range to converted values over the output range using the first and second limit values.

10. The method of claim 9, wherein the population is identified in step (d) by reference to a desired threshold log-transformed value.

11. The method of claim 10, comprising the further step of comparing the identified output range to a desired output range, and modifying the desired threshold log-transformed value based upon the comparison.

12. The method of claim 11, wherein the desired output range is determined based upon the lower limit value.

13. The method of claim 9, wherein the lower limit value is identified based upon a value below which values of a desired fractional portion of the pixels fall.

14. A method for determining a useful range of image pixel intensity values in a digital pixel imaging system, the method comprising the steps of:

(a) determining a lower limit value of the useful range by identifying an intensity value below which non-log transformed values of a desired fractional portion of the pixels fall;

(b) generating an intensity histogram and a log-transformed histogram based upon the intensity histogram;

(c) identifying a threshold value for an upper limit value based upon the log-transformed histogram;

(d) identifying a population of pixels having log-transformed values having a desired relationship to the threshold value; and (e) determining an upper limit value of the useful range based upon the identified population.

15. The method of claim 14, wherein the population identified in step (d) is a population having log-transformed values lower than the threshold value.

16. The method of claim 14, wherein the lower limit value is determined based upon a population of pixels identified in the intensity histogram.

17. The method of claim 16, wherein the upper limit value is determined based upon the log-transformed histogram and the population identified in step (d).

18. The method of claim 14, wherein the threshold value corresponds to a desired log-transformed value.

19. The method of claim 18, wherein the population identified in step (d) is identified by comparison of the threshold value to log-transformed values in the log-transformed histogram.

20. The method of claim 14, including the further steps of comparing the population identified in step (d) to a desired population size, and resetting the threshold value based upon the comparison.

* * * * *